United States Patent
Sorres et al.

(12) 
(10) Patent No.: US 12,178,790 B2
(45) Date of Patent: Dec. 31, 2024

(54) **ANTIBACTERIAL COMPOUND ISOLATED FROM *PSILOXYLON MAURITIANUM* AND ITS DERIVATIVES**

(71) Applicants: CENTRE NATIONAL DE LA RECHERCHE SCIENTIFIQUE(CNRS), Paris (FR); Jonathan Sorres, Saint Pierre (FR)

(72) Inventors: Jonathan Sorres, Saint Pierre (FR); Véronique Eparvier, Gif-sur-Yvette (FR)

(73) Assignees: Jonathan Sorres, Saint Pierre (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 209 days.

(21) Appl. No.: 17/394,572

(22) Filed: Aug. 5, 2021

(65) Prior Publication Data
US 2023/0062900 A1    Mar. 2, 2023

(51) Int. Cl.
| | | |
|---|---|---|
| *A61K 31/122* | (2006.01) | |
| *A61K 8/35* | (2006.01) | |
| *A61K 38/12* | (2006.01) | |
| *A61P 31/04* | (2006.01) | |
| *A61P 31/10* | (2006.01) | |
| *A61Q 19/00* | (2006.01) | |
| *A61Q 19/02* | (2006.01) | |
| *A61Q 19/08* | (2006.01) | |
| *C07C 45/78* | (2006.01) | |

(52) U.S. Cl.
CPC ............ *A61K 31/122* (2013.01); *A61K 8/35* (2013.01); *A61K 38/12* (2013.01); *A61P 31/04* (2018.01); *A61P 31/10* (2018.01); *A61Q 19/007* (2013.01); *A61Q 19/02* (2013.01); *A61Q 19/08* (2013.01); *C07C 45/783* (2013.01)

(58) Field of Classification Search
CPC ........ A61K 31/122; A61P 31/10; A61Q 19/08
See application file for complete search history.

(56) References Cited

U.S. PATENT DOCUMENTS

2011/0257078 A1* 10/2011 Young .................... A61K 31/42
514/2.7

OTHER PUBLICATIONS

Li, N., et al. Res. Microbiol. (2014), 165; 263-272.*
Mahomoodally, M. F., et al. J. Intercult. Enthopharmacol. (2014), 3(4); 192-195.*
Mahomoodally et al. Psiloxylon mauritianum (Bouton ex Hook.f.) Baillon (Myrtaceae): A promising traditional medicinal plant from the Mascarene Islands, Ethnopharmacology, Aug. 2014, pp. 1-4 (Year: 2014).*
Sorres et al. Potent and Non-Cytotoxic Antibacterial Compounds Against Methicillin-Resistant *Staphylococcus aureus* Isolated from Psiloxylon mauritianum, A Medicinal Plant from Reunion Island, Molecules 2020, 25, 3565, 1-8.
Socolsky et al. Fern Acylphloroglucinols: Structure, Location, and Biological Effects, Studies in Natural Products Chemistry, 2012, 38, 5, 105-157.

* cited by examiner

*Primary Examiner* — Sarah Pihonak
*Assistant Examiner* — Mikhail O'Donnel Robinson
(74) *Attorney, Agent, or Firm* — Arrigo, Lee, Guttman & Mouta-Bellum LLP (57) ABSTRACT

Aspidin BB derivatives, compositions containing them, and methods of making and using them.

11 Claims, 1 Drawing Sheet

ANTIBACTERIAL COMPOUND ISOLATED FROM *PSILOXYLON MAURITIANUM* AND ITS DERIVATIVES

The present invention relates to anti-microbial compounds. In particular, it concerns a method of treatment of infections caused by antibiotic-resistant *Staphylococcus aureus* strains such as a methicillin-resistant *Staphylococcus aureus* or by other bacteria such *E. coli* or *Acinetobacter baumannii* for which no treatment is available so far.

BACKGROUND OF THE INVENTION

*Staphylococcus aureus* is a Gram-positive bacterium and the major cause of hospital-acquired infections, often resulting in longer stays and increases in patient mortality. Such *S. aureus* infections, promoted by the use of ventilators or venous catheters, affect the bloodstream, lower respiratory tract, and the skin and soft tissues. The microbial world is ruled by adaptation to environmental pressure, and *S. aureus* has developed very effective tools to resist antibiotics since the introduction of penicillin in the 1940s to cure infections. The selective pressure of antibiotics continually promotes the emergence of drug-resistant strains of *S. aureus*, which have dramatically increased and spread around the world.

Methicillin-resistant *Staphylococcus aureus* (MRSA) emerged quickly after introduction of the first semi-synthetic β-lactam in 1961 and has become a major worldwide health care problem. Due to the rapidity and extent of its spread, as well as the high diversity among clones and strain virulence, the WHO has classified MRSA as a high priority target for new antibiotic development.

Even if pharmaceutical companies prefer combinatorial chemistry library strategies, the large diversity of natural products offers a wide range of antimicrobials. Plant sources of anti-staphylococcal compounds should be highlighted due to reports in the literature of remarkable activities of acylphloroglucinols or terthiophenes, which have minimum inhibitory concentrations (MIC) of less than 1 µg/mL.

*Psiloxylon mauritianum* Baill. is a dioecious glabrous flowering plant classified as a member of the Myrtaceae family and is a unique species of the genus *Psiloxylon*. *P. mauritianum* is endemic to Reunion Island and Mauritius and used there as a medicinal plant for the treatment of common infectious and inflammatory diseases, hypercholesterolemia, gout, dysentery and to alleviate symptoms of amenorrhea. In 2013, the leaves of *P. mauritianum* were listed in the French pharmacopoeia and constitute one of the best-selling medicinal plants on Reunion Island. Aqueous extracts of *P. mauritianum* have also demonstrated antiviral activity against strains of Zika and Dengue viruses in vitro, without exhibiting genotoxic effects, in several mammalian cell types. The crude acetone extract of *P. mauritianum* was found to harbor antioxidant activity and showed antimicrobial activity, with an MIC of 51 µg/mL recorded against *S. aureus*. Through bioassay guided fractionation, this anti-staphylococcal activity was linked to the presence of corosolic and asiatic acids. Despite its promising biological activities and a large consumption of the leaf infusions by Reunionese people, very few phytochemical studies were found in the literature, and to date, only the two pentacyclic triterpenes mentioned above have been isolated from *P. mauritianum*.

There is a need for identification of new compounds with anti-bacterial activity, especially against *S. aureus*, but also against other bacteria for which no inhibitor is available.

SUMMARY OF THE INVENTION

In an effort to identify new natural antimicrobial compounds and to explore the chemical diversity of plants from Reunion Island, the inventors first demonstrated that the ethyl acetate extract (EtOAc) from *P. mauritianum* demonstrated strong antimicrobial activity against *S. aureus* (MIC of 8 µg/mL), and especially that this activity is supported by aspidin BB, but also by a newly identified aspidin, called aspidin CB presenting even a better antibacterial activity than aspidin BB.

The invention thus concerns a method of treating of a microbial infection, the method comprising administrating a composition comprising an aspidin BB derivatives of formula (I)

in a patient in need thereof.

The microbial infection can be caused by a bacterium strain.

The microbial infection can be caused by a gram-positive bacterium strain, in particular an antibiotic resistant gram-positive bacterium strain such as methicillin-resistant *Staphylococcus aureus* or a vancomycin-resistant *Staphyloccocus aureus*.

The microbial infection can also be caused by a gram-negative bacterium strain, in particular an *Acinetobacter baumannii* strain. For the treatment of gram-negative bacteria caused infection, the method can further comprise the administration of at least one outer membrane permeabilizer, such as polymyxins.

The invention also concerns an antimicrobial composition against Gram-negative bacterium such as *Escherichia coli*, *Klebsiella pneumoniae*, *Acinetobacter baumannii*, *Pseudomonas aeruginosa*, and *Enterobacter* spp, comprising an aspidin compound of formula (I) in combination with an outer membrane permeabilizer such as polymyxins.

It is another aspect of this invention to propose a method of treating a fungal infection using an aspidin of formula (I).

In a preferred embodiment, the aspidin of formula (I) is an aspidin CB of formula (II). The aspidin of formula (II) as such is an object of the invention.

The invention also concerns two different methods of extraction of aspidin compounds of formula (I), one using organic solvent, the other using supercritical $CO_2$.

The invention also concerns a method of preparation of a cosmetic composition comprising the steps of mixing:
  (i) at least one preservative agent which is an aspidin BB derivatives of formula (I)
  (ii) at least one agent chosen among a moisturizing agent, an anti-aging agent, a slimming agent, a whitening agent . . .
and a cosmetic composition resulting from such method.

ADVANTAGES OF THE INVENTION

This invention provides new aspidin compounds with antibacterial properties. Especially, aspidin CB presents an antibacterial activity which is superior to aspidin BB.

Further, the invention proposes for the first time the use of aspidin of formula (I) (including some known aspidins) in a method of treatment of bacterial infections. This proposal broadens the medical tools available for clinicals to overcome unmeet medical needs.

Interestingly, the aspidins of formula (I) present a higher antibacterial activity than aspidin BB. Especially, aspidin CB is a promising drug to fight pathologic bacteria, including antibiotic-resistant *Staphylococcus aureus*. Further, aspidin CB allows, in combination with colistin, to treat infections due to gam-negative bacteria such as *E. coli* or *Acinetobacter baumannii* for which new and efficient inhibitors are expected. Positive results—presented in the experimental part—already validate the efficacy of aspidin CB on the inhibition of different clinical strains.

The invention provides two methods for extracting aspidin from plants, in particular from *Psiloxylon mauritianum*. One of this method does not use organic solvent; this ecological method permits to obtain aspidin molecules that are non-toxic and that can thus be used in cosmetic, as preservative, for their antibacterial and/or antioxydant properties.

DETAILED DESCRIPTION OF THE INVENTION

A first object of the invention concerns a method of treatment of a microbial infection consisting in administrating a composition comprising an aspidin BB derivatives of formula (I)

(I)

wherein
n is from 0 to 16
R2 an R3 are selected from the group consisting of hydrogen, OH, Oalkyl, Oaryl, $NH_2$, NHalkyl, NHaryl, N(alkyl)$_2$, N(aryl)$_2$, alkyl,
R1 and R4 are selected from selected group from the group consisting of, OH, Oalkyl, Oaryl, $NH_2$, NHalkyl, NHaryl, N(alkyl)$_2$, N(aryl)$_2$, alkyl, SH, Salkyl, $SO_2H$,
G1 and G2 are selected from the group consisting of OH, Oalkyl, $NH_2$, NHalkyl, NHaryl, N(alkyl)$_2$, N(aryl)$_2$, SH
G3, G4n G5, G6 are selected from the group consisting of hydrogen, Cl, BR, F, I, NO2, CN, $NH_2$, NHalkyl, NHaryl, N(alkyl)$_2$, N(aryl)$_2$, SH, Salkyl, sulfate.
to a patient in need thereof.

In a preferred embodiment of the invention, the aspidin BB derivative is a compound formula (II)

(II)

In a particular embodiment, the aspidin derivatives used in the method of the invention is a compound of formula (I) excluding aspidin CB of formula (II).

As used herein, the terms "treating" mean that the microbial load in a patient is reduced by at least 20%, preferably by 50% to 80% and mostly preferred by 100% so that the patient is cured.

The microbial infection to be treated by aspidin BB derivatives of formula (I) can be caused by a bacterium. This bacterium can be either a gram-positive or a gram-negative bacterium strain.

The antibacterial activity is evaluated by measuring the minimal inhibitory concentration (MIC). It is considered that a compound presents an antibacterial activity when the MIC is at least 256 µg/mL, or at least 128 µg/mL, even at least 64 µg/mL, and preferably at least 32 µg/mL.

The gram-positive bacterium strain can be chosen among the following strains: *Staphylococcus aureus, S. epidermdis, Staphylococcus hominis, Staphylococcus argenteus, Staphylococcus haemolyticus, Staphylococcus warnieri, Staphylococcus lugdunensis, Corynebacterium diphteriae, Corynebacterium minutissimurn, Corynebacterium acnes* (*Propionibacterium acnes*), *Corynebacterium* sp., *Bacillus cereus, Bacillus subtilis, Bacillus anthracis, Bacillus* sp., *Enterococcus faecium, Enterococcus faecalis, Enterococcus* sp *Nocardia abscessus, Nocardia farcinica, Nocardia asteroides, Nocardia cyriacigeorgica, Nocardia brasiliensis, Nocardia brevicatena, Nocardia paucivorans, Nocardia nova, Nocardia transvalensis, Nocardia* sp. *Streptococcus pyogenes, Streptococcus agalactiae, Streptococcus pneumoniae, Streptococcus mutans, Streptococcus* sp.

In particular, the *Staphylococcus aureus* strain can be a methicillin-resistant *Staphylococcus aureus* or a vancomycin-resistant *Staphyloccocus aureus*.

The gram-negative bacterium strain can be chosen among the following strains: *Escherichia coli, Klebsiella pneumoniae, Acinetobacter baumannii, Pseudomonas aeruginosa,* and *Enterobacter* spp.

For the treatment of gram-negative strain, the method can further comprising the administration of at least one outer membrane permeabilizer such as polymyxins, in particular colistin (also known as polymyxin E). In a preferred embodiment of the invention, the method of treatment of an infection caused by a gram-negative bacteria comprises the administration of an aspidin of formula (I) with outer membrane permeabilizer. Mostly preferred is the administration of aspidin CB with colistin.

A second object of the invention concerns an antimicrobial composition against Gram-negative bacterium such as *Escherichia coli, Klebsiella pneumoniae, Acinetobacter baumannii, Pseudomonas aeruginosa,* and *Enterobacter* spp, comprising an aspidin compound of formula (I) in combination with an outer membrane permeabilizer such as polymyxins, in particular colistin. In a preferred embodiment, the apsidin compound present in the composition is aspidin CB of formula (II)

The microbial infection to be treated by aspidin BB derivatives of formula (I) can be caused by a fungi. Such fungi can be part of the following list: *Candida albicans, Candida parapsilosis, Candida glabrata, Candida tropicalis, Cryptococcus neoformans, Cryptococcus gatti, Pneumocystis jirovecii, Aspergillus fumigatus, Aspergillus flavus, Aspergillus nidulans, Aspergillus versicolor, Aspergillus niger, Aspergillus terreus, Histoplasma capsulatum, H. capsulatum duboisii, Torulopsis glabrata*.

A third object of the invention is an aspidin BB derivative of formula (II)

(II)

This newly described aspidin is called aspidin CB.

Aspidins are molecules of the family of acylphloroglucinols which occur mainly in ferns of the genera *Dryopteris, Arachniodes* and *Elaphoglossum*. The presence of these compounds has also been reported from a few species belonging to the genera *Stigmatopteris, Dryopsis, Polystichum, Psiloxylacaeae, Rumohra, Nothoperanema, Lastreopsis, Polybotrya, Acrophorus, Ctenitis, Pleocnemia,* and *Peranema*.

Thus, the method of extracting aspidin of the invention can be applied to plant of the genera *Dryopteris, Arachniodes, Elaphoglossum, Stigmatopteris, Dryopsis, Polystichum, Psiloxylacaeae, Rumohra, Nothoperanema, Lastreopsis, Polybotrya, Acrophorus, Ctenitis, Pleocnemia,* and *Peranema*.

A fourth object of the invention concerns a method of extracting an aspidin of formula (I) from a plant chosen among the genera *Dryopteris, Arachniodes, Elaphoglossum, Stigmatopteris, Dryopsis, Polystichum, Psiloxylacaeae, Rumohra, Nothoperanema, Lastreopsis, Polybotrya, Acrophorus, Ctenitis, Pleocnemia,* and *Peranema*, including the steps of:

Drying the plant leaves at room temperature
Crushing the dried leaves
Macerating the crushed plant with an organic solvent
Collecting the organic solvent
Purifying the aspidin by chromatography.

The organic solvent can be for example EtOAc, DCM, $Et_2O$ as well as any other appropriate solvents well known from a skilled person in the art.

A fifth object of the invention concerns a method of extracting an aspidin of formula (I) from a plant chosen among the genera *Dryopteris, Arachniodes, Elaphoglossum, Stigmatopteris, Dryopsis, Polystichum, Psiloxylacaeae, Rumohra, Nothoperanema, Lastreopsis, Polybotrya, Acrophorus, Ctenitis, Pleocnemia,* and *Peranema*, including the steps of:

Drying the plant leaves at room temperature
Grinding the dried leaves
Extracting the dried leave powder with supercritical $CO_2$ using or not ethanol as co-solvent;
Collecting the organic phase and removing the residual solvent under reduced pressure.

This method of extracting aspidin can be qualified as "green" since it does not involve the use of organic solvent. The resulting molecule are thus free of any toxic residue. In particular, such method allows to use the extracted aspidin in cosmetic field. The 12 principles of green chemistry are described in Anastas, P. T.; Warner. J. C. *Green Chemistry: Theory and Practice,* Oxford University Press: New York, 1998, p.30.

Grinding can be performed using any known method, for example by dry grinding at room temperature or with liquid nitrogen.

Ethanol is not necessary for extracting aspidin BB or CB but can be useful for extracting other aspidins. Further, ethanol can be used for improving elution of the molecule (even if not used for extraction).

In a preferred embodiment of the invention, the plant used to extract aspidin is *Psiloxylon mauritianum*.

These two methods allow to extract all known natural aspidins of formula (I). These aspidins are in particular the following compounds:

(III)

Especially:
Albaspidin AA—$R_1=R_2=CH_3$
Albaspidin AB—$R_1=CH_3$, $R_2$=n-Pr
Albaspidin BB—$R_1=R_2$=n-Pr
Albaspidin PB—$R_1$=Et, $R_2$=n-Pr
Albaspidin PP—$R_1=R_2$ =Et
Albaspidin AP—$R_1=CH_3$, $R_2$ =Et
Albaspidin iBiB—R =i-Pr
Albaspidin BV—$R_1$=n-Pr, $R_2$=n-$C_4H_9$
Albaspidin iBV—$R_1$=i-Pr, $R_2$=n-$C_4H_9$
Albaspidin VV—$R_1=R_2$ =n-$C_4H_9$ (IV)

especially :
Norflavaspidic acid AB—$R_1=CH_3$, $R_2$=n-Pr
Norflavaspidic acid BB—$R_1=R_2$=n-Pr
Norflavaspidic acid AP—$R_1=CH_3$, $R_2$=Et
Norflavaspidic acid PB—$R_1$=Et, $R_2$=n-Pr (V)

especially
Flavaspidic acid AB—$R_1=CH_3$, $R_2$ =n-Pr
Flavaspidic acid BB—$R_1=R_2$=n-Pr
Flavaspidic acid AP—$R_1=CH_3$, $R_2$=Et
Flavaspidic acid PA—$R_1$=Et, $R_2=CH_3$
Flavaspidic acid PB—$R_1$=Et, $R_2$=n-Pr Flavaspidic acid BP—$R_1$=n-Pr, $R_2$=Et
Flavaspidic acid PP—$R_1$=$R_2$=Et
Flavaspidic acid VV—$R_1$=$R_2$ =n-$C_4H_9$
Flavaspidic acid VB—$R_1$=n-$C_4H_9$, $R_2$=n-Pr
Flavaspidic acid BV—$R_1$=n-Pr, $R_2$ =n-$C_4H_9$ especially
iso-aspidin AB—$R_1$=$CH_3$, $R_2$=n-Pr
iso-aspidin BB—$R_1$=$R_2$=n-Pr
iso-aspidin PB—$R_1$=Et, $R_2$=n-Pr

(VI)

(IX)

especially
Aspidin AA—$R_1$=$R_2$=$CH_3$
Aspidin AB—$R_1$=$CH_3$, $R_2$=n-Pr
Aspidin BB—$R_1$=$R_2$=n-Pr
Aspidin AP—$R_1$=$CH_3$, $R_2$=Et
Aspidin PA—$R_1$=Et, $R_2$=$CH_3$
Aspidin PB—$R_1$=Et, $R_2$=n-Pr
Aspidin BP—$R_1$=n-Pr, $R_2$=Et
Aspidin PP—R-$R_1$=$R_2$=Et
Aspidin iBiB—$R_1$=$R_2$=i-Pr
Aspidin VB—$R_1$=n-$C_4H_9$, $R_2$=n-Pr
Aspidin iBB—$R_1$=i-Pr, $R_2$=n-Pr especially
Desaspidin AB—$R_1$=$CH_3$, $R_2$=n-Pr
Desaspidin BA—$R_1$=n-Pr, $R_2$=$CH_3$
Desaspidin BB—$R_1$=$R_2$=n-Pr
Desaspidin PB—$R_1$=Et, R2=n-Pr
Desaspidin AP—$R_1$=CH3, R2=Et
Desaspidin PA—$R_1$=Et, R2=CH3
Desaspidin PP—$R_1$=R2=Et
Desaspidin VV—$R_1$=R2=n-$C_4H_9$
Desaspidin VB—$R_1$=n-$C_4H_9$ $R_2$ =n-Pr
Desaspidin BV—$R_1$=n-Pr $R_2$=n-$C_4H_9$

(VII)

(X)

Ortho-desaspidin BB—$R_1$=$R_2$=n-Pr especially
Para-aspidin AA—$R_1$=$R_2$=$CH_3$
Para-aspidin AB—$R_1$=$CH_3$, $R_2$=n-Pr
Para-aspidin BB—$R_1$=$R_2$=n-Pr
Para-aspidin AP—$R_1$=$CH_3$, $R_2$=Et
Para-aspidin PA—$R_1$=Et, $R_2$=$CH_3$
Para-aspidin BP—$R_1$=n-Pr, $R_2$=Et
Para-aspidin PB—$R_1$=Et, $R_2$=n-Pr
Para-aspidin PP—$R_1$=$R_2$=Et (XI)

(VIII)

especially
Phloraspin BB—$R_1$=$R_2$=n-Pr
Phloraspin PB—$R_1$=Et, $R_2$=n-Pr
Phloraspin BP—$R_1$=n-Pr, $R_2$=Et
Phloraspin PP—$R_1$=$R_2$=Et
Phloraspin VB—$R_1$=n-$C_4H_9$, $R_2$=n-Pr
Phloraspin BV—$R_1$=n-Pr, $R_2$=n-$C_4H_9$
Phloraspin VV—$R_1$=$R_2$=n-$C_4H_9$ A sixth object of the invention concerns a method of preparing a cosmetic composition comprising the steps of mixing:
(iii) at least one preservative agent which is an aspidin BB derivatives of formula (I)

(iv) at least one cosmetic ingredient such as a moisturizing agent, an anti-aging agent, a slimming agent, a whitening agent . . .

A seventh object of the invention concerns a cosmetic composition comprising (i) at least one preservative agent which is an aspidin BB derivatives of formula (I) and (ii) at least one agent chosen among a moisturizing agent, an anti-aging agent, a slimming agent, a whitening agent . . . This composition can be prepared by the method previously described.

Such composition can further comprise any formulation ingredients such as emollients, texturing agents, surfactants . . .

In a preferred embodiment, in the method of preparation of a cosmetic composition as well as in the cosmetic composition itself, said aspidin is aspidin CB represented by formula (II).

EXAMPLES

I—Materials and Methods

General Experimental Procedures

Nuclear magnetic resonance (NMR) spectra were recorded on a Bruker 500 MHz spectrometer or on a Bruker 700 MHz spectrometer equipped with 5 mm inverse detection Bruker. Chemical shifts (δ) are reported in ppm based on the signal for TMS. Chemical shifts were referenced using the corresponding solvent signals ($\delta_H$ 2.05 and $\delta_C$ 29.92 for $(CD_3)_2CO$). HRESIMS measurements were performed using a Waters Acquity UHPLC system with a column bypass coupled to a Waters Micromass LCT Premier time-of-flight mass spectrometer equipped with an electrospray interface (ESI). X-ray diffraction data for compound 1 were collected on the PROXIMA 2A (PX2A) beamline at the SOLEIL Synchrotron, Gif-sur-Yvette, Paris, France. They were indexed, integrated with XDS and scaled with AIMLESS, as implemented within the autoProc toolbox. For compound 2, data were collected using redundant ω scans on a Rigaku XtaLabPro single-crystal diffractometer using microfocus Mo Kα radiation and a HPAD PILATUS3 R 200K detector. Its structure was readily solved by intrinsic phasing methods (SHELXT) and by full-matrix least-squares methods on F2 using SHELX-L. The non-hydrogen atoms were refined anisotropically, and hydrogen atoms, identified in difference maps, were positioned geometrically and treated as riding on their parent atoms. Molecular graphics were computed with Mercury 4.3.0. Flash chromatography was performed on a Grace Reveleris system with dual UV and ELSD detection equipped with a 40 g $C_{18}$ column. Preparative HPLCs were conducted with a Gilson system equipped with a 322 pumping device, a GX-271 fraction collector, a 171 diode array detector, and a prepEL-SII detector electrospray nebulizer. The columns used for these experiments included a Phenomenex Kinetex C8 5 µm 4.6 x 250 mm analytical column and Phenomenex Kinetex C8 5 µm 21.2×250 mm preparative column. The flow rate was set to 1 or 21 mL/min, respectively, using a linear gradient of $H_2O$ mixed with an increasing proportion of $CH_3CN$. Both solvents were of HPLC grade, modified with 0.1% formic acid.

Plant Material

Leaves of *Psiloxylon mauritianum* Baill. (Myrtaceae) were collected in Les Avirons, Reunion Island in 2016, identified by Raymond Lucas (Association APN, Réunion). A voucher specimen was deposited at ICSN-CNRS.

Extraction and Isolation

After collection, plant material was air dried in the shade at room temperature. Crushed dried leaves (135 g) were extracted by maceration with EtOAc (2×0.7L,2×24h) on a rotary shaker (90 rpm). The organic solvent was collected by vacuum filtration and concentrated to dryness under reduced pressure to yield 10.6 g of extract. A portion of the extract (1.2 g) was subjected to reverse phase flash chromatography using a gradient of $H_2O$ mixed with an increasing proportion of $CH_3CN$, both with 0.1% formic acid, to afford 14 fractions (A to N). A portion of fraction I (10 mg), eluted with 100% $CH_3CN$, was subjected to preparative HPLC (isocratic elution at 20:80) to afford the mixture ursolic acid 3: oleanic acid 4 (6:4) (2.4 mg, RT =6.0 min), and Aspidin BB 1 (4.3 mg, RT=12.5 min). A portion of fraction J (40 mg) was washed with cold MeOH (0° C.) to afford Aspidin CB 2 (20 mg). After NMR experiments, small crystal needles were observed in samples tubes of Aspidin BB 1 and Aspidin CB 2.

These crystals were carefully collected and analyzed by X ray crystallography.

Aspidin BB (1): White amorphous solid or colorless crystal needles; $^1$H-NMR (500 MHz, $(CD_3)_2CO$: $\delta_H$ 3.80 (3H, s, H7), 3.57 (2H, s, H7), 3.18 (2H, dd, J=7.3, 7.3 Hz, H9), 3.15 (2H, dd, J=7.2, 7.2 Hz, 2H), 2.10 (3H, s, H12), 1.70 (4H, m, H10, H10), 1.49 (6H, s, H12, H13), 1.00 (3H, t,J=7.4 Hz, H11), 0.98 (3H, t, J=7.4 Hz, H11); $^{13}$C-NMR (125 MHz, $(CD_3)_2CO$: $\delta_C$ 208.0 (C8), 207.4 (C8), 199.8 (C4), 188.4 (C2), 172.7 (C6), 163.6 (C6), 161.5 (C4), 160.3 (C2), 113.1 (C5), 111.8 (C1), 110.2 (C1), 109.0 (C3), 108.5 (C3), 62.1 (C7), 45.0 (C5), 44.4 (C9), 43.5 (C9), 25.1 (C12), 25.1 (C13), 18.8 (C10), 18.2 (C10), 17.7 (C7), 14.2 (C11), 14.1 (C11), C12 (9.5); HRESIMS [M +H]$^+$m/z 461.2173 (calc. for $C_{25}H_{33}O_8$, 461.2175).

Aspidin CB (2): White amorphous solid or colorless crystal needles; $^1$H-NMR (500 MHz, $(CD_3)_2CO$ and $^{13}$C-NMR (125 MHz, $(CD_3)_2CO$) see Table 1; HRESIMS [M+H]$^+$ m/z 489.2490 (calculated for $C_{27}H_{37}O_8$, 489.2488).

Ursolic acid (3): oleanicacid (4) (6:4 mixture): White amorphous; $^1$H-NMR (700 MHz, $(CD_3)_2CO$ and $^{13}$C-NMR (175 MHz, $(CD_3)_2CO$) see Table HRESIMS [M+ H]$^+$ m/z 457.3661 (calculated for $C_{30}H_{49}O_3$, 457.3682).

Organic Extractions

Crushed dried leaves (250 g) were extracted by maceration with EtOAc (0.7 L, during 24 h, twice) on a rotary shaker (90 rpm). The organic solvent was collected by vacuum filtration and concentrated to dryness under reduced pressure to yield 10.6 g of EtOAc extract. A successive maceration was realized with MeOH (0.7 L, during 24 h, twice) on a rotary shaker (90 rpm). The organic solvent was collected by vacuum filtration and concentrated to dryness under reduced pressure to yield 42 g of MeOH extract. Crushed dried stems (135 g) were extracted by maceration with the same procedure described above to yield 1.3 g of EtOAc extract and 5.5 g of MeOH extract.

Aqueous Extractions

Crushed dried leaves (10 g) were added to 200 ml of deionized water at 100° C. on a rotary shaker (90 rpm) for 15 min. The material was the infused for 2-16 h. The aqueous phase was collected by vacuum filtration and concentrated to dryness under reduced pressure to yield 2.2 g of water extract. Crushed dried stems (1.0 g) were extracted by maceration with the same procedure described above to yield 1.2 g of water extract.

Fractionation of Methanolic Extract

A portion of the extract (1.2 g) was subjected to reverse phase flash chromatography using a gradient of H2O mixed with an increasing proportion of CH3CN, both with 0.1% formic acid, to afford 70 fractions (1 to 70).

Green Extraction: SFE-$CO_2$ Extracts from *Psiloxylon mauritianum*

Supercritical Fluid Extractions (SFE) were performed on a 1260 Infinity Analytical SFC system (Agilent Technologies, Waldbronn, Germany) consisting of an Aurora module and an "LC-like" system. This one was equipped with a pumping system, which allows adding modifier to $CO_2$. A stainless steel cylindrical extraction cells located in the oven at 50° C. with a 100×4.6 mm (0.5 mL) were used for the SFE extraction. The extraction cell was fully filled with the plant powder. UHPLCs were conducted with a Shimadzu Nexera X2 system equipped, diode array detector and a SEDEX Model 90 LT-ELSD detector. The column used for these experiments was a Phenomenex Kinetex XB-C18 1.7 µm, 150*2.1 mm. The flow rate was set to 0.6 mL/min using a linear gradient of $H_2O$ mixed with an increasing proportion of $CH_3CN$. Both solvents were of HPLC grade, modified with 0.1% formic acid.

Determination of Minimal Inhibitory Concentration: Antibacterial Properties

The crude extract and pure compounds isolated were tested against human pathogenic microorganisms, including the bacterium *Staphylococcus aureus* (ATCC 29213), MRSA (ATCC 33591), *Candida albicans* (ATCC 10213), *Trichophyton rubrum* (SNB-TR1) and *P. aeruginosa* ATCC 27853 to screen their antibacterial and antifungal activities. All ATCC strains were purchased from the Pasteur Institute. The clinical isolate was provided by Prof. Philippe Loiseau, Université Paris Sud. The ITS sequence was deposited in the NCBI GenBank database under the registry number KC692746 corresponding to SNB-TR1 strain. The tests were conducted in accordance to the reference protocols from the European Committee on Antimicrobial Susceptibility Testing. The standard microdilutions, ranging from 256 to 0.25 µg/mL were made from stock solutions prepared in DMSO (Sigma-Aldrich, France). The microplates were incubated at 35° C., and MIC values were obtained after 48 h for C. albicans, 24 h for *S. aureus* and 5 days for *T. rubrum*. The MIC values reported in Table 2 refer to the lowest concentration preventing visible growth in the wells. Vancomycin (Sigma-Aldrich, Saint-Quentin Fallavier, France) and oxacillin (Sigma-Aldrich, Saint-Quentin Fallavier, France) were used as positive controls for bacteria. Fluconazole (Sigma-Aldrich, Saint-Quentin Fallavier, France) and itraconazole (Sigma-Aldrich, Saint-Quentin Fallavier, France) were used as positive controls for fungi. All assays were conducted in duplicate.

Cytotoxicity Evaluation

Human lung fibroblast cells (MRC-5) were purchased from ATCC (Rockville, Md., USA) and cultured as recommended. Cell growth inhibition was determined by an MTS assay according to the manufacturer's instructions (Promega, Madison, Wis., USA). The cells were seeded in 96-well plates containing the growth medium. After 24 h of culture, samples were dissolved in DMSO (Sigma-Aldrich, France), and added to the cells (at 1 and 10 µM final concentrations). After 72 h of incubation, the reagent was added, and the absorbance at 490 nm was recorded using a plate reader. Cell viability was evaluated in comparison with untreated control cultures. Docetaxel (Taxotere) was used as positive control ($IC_{50}$: 0.5 nM). All assays were conducted in triplicate.

Antioxidant Evaluation

*P. mauritianum* extracts were investigated for their antioxidant activities with using an ABTS [2,2'-azinobis-(3-ethylbenzothiazoline-6-sulfonate)] assay.

II—Isolation of Compounds in the Antibacterial EtOAc Plant Extract

Figure 1:
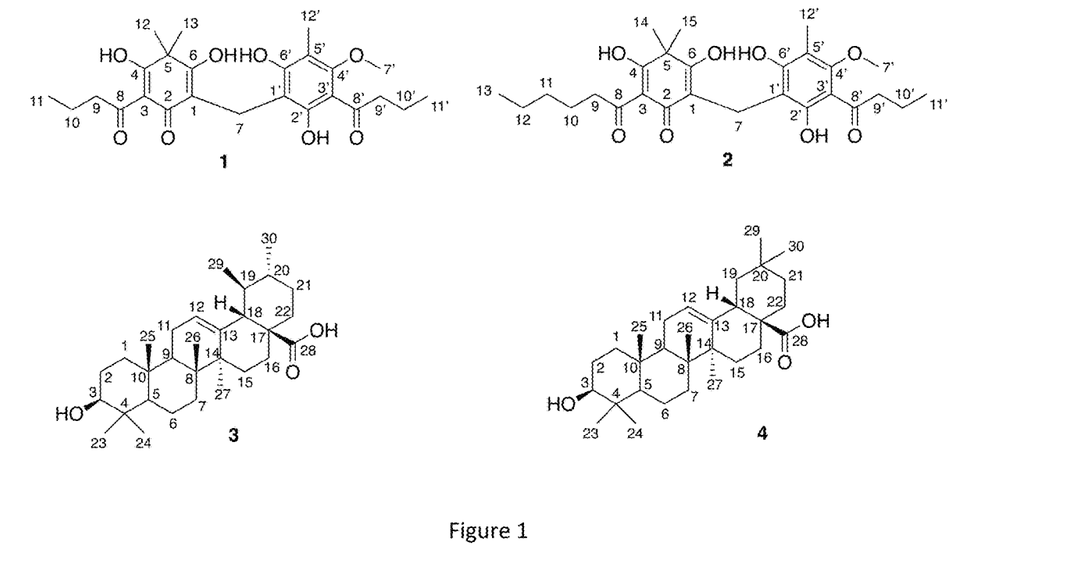
FIG. 1. Structure of the compounds isolated from *Psiloxylon mauritianum*.

Bioassay guided fractionation of the extract of *Psiloxylon mauritianum* led to isolation of the known molecules Aspidin BB (1), ursolic acid (3) and oleanic acid (4), along with compound 2 that had not previously been isolated or described in the literature (FIG. 1). The known compounds were identified by comparison of $^1$H and $^{13}$C data with values reported in the literature, together with crystallography data for 1. The common triterpenic acids 3 and 4 were isolated as a 6:4 ratio mixture, and the complete $^1$H and $^{13}$C-NMR assignments were deduced from NMR 1D and 2D experiments conducted on a 700 MHz NMR spectrometer.

Compound 2 was initially obtained as a white amorphous solid. HRESIMS analysis of 2 revealed a molecular formula of $C_{27}H_{36}O_8$ (m/z 489.2490 for [M+H]$^+$), implying 2 C and 4 H more than in Aspidin BB 1. The $^1$H-NMR spectrum displayed remarkably downfield-shifted singulet signals at $\delta_H$ 15.86, 11.41 and, 10.05, which are characteristic of the hydroxyl groups found in acylphloroglucinols Aspidin derivatives. The $^1$H-NMR data of 2 were very similar to those for 1 except for the presence of a supplementary signal at $\delta_H$ 1.39 (m) integrating four protons (H11 and H12), and a two methyl triplet at $\delta_H$ 0.98 (J=7.4 Hz) and $\delta_H$ 0.93 (J=7.1 Hz), which are the common signals for methyl terminal groups (Table 1).

TABLE 1

The 1D and 2D NMR data for Aspidin CB (2) in acetone-$d_6$.

| | Aspidin CB | | | | |
|---|---|---|---|---|---|
| Position | $\delta_c{}^1$ | $\delta_H$ (J in Hz)$^2$ | COSY | HMBC | ROESY |
| 1 | 111.9 | | | | |
| 2 | 188.4 | | | | |
| 3 | 108.9 | | | | |
| 4 | 199.9 | | | | |
| 5 | 45.1 | | | | |
| 6 | 172.7 | | | | |
| 7 | 17.7 | 3.57, s | | C1, C2, C6, C1', C2', C6' | |
| 8 | 207.5 | | | | |
| 9 | 41.6 | 3.19, dd (7.2, 7.2) | H8 | C3, C8, C10, C11 | H11 |
| 10 | 25.3 | 1.67, m | H9, H11 | C8, C9, C11, C12 | |
| 11 | 32.5 | 1.39, m | H10, H12 | C12 | H9 |
| 12 | 23.2 | 1.38, m | H11, H13 | C11 | |
| 13 | 14.3 | 0.93, t (7.1) | H12 | C11, C12 | |
| 1' | 110.2 | | | | |
| 2' | 160.6 | | | | |
| 3' | 108.5 | | | | |
| 4' | 161.5 | | | | |
| 5' | 113.2 | | | | |
| 6' | 163.6 | | | | |
| 7' | 62.1 | 3.80, s | | C4' | H9' |
| 8' | 208.0 | | | | |
| 9' | 44.8 | 3.15, dd (7.2, 7.2) | H10' | C8', C10', C11' | H7' |
| 10' | 18.8 | 1.72, sex (7.4) | H9', H11' | C8', C10', C11' | |
| 11' | 14.2 | 0.98, t (7.4) | H10' | C9', C10' | H9' |
| 12' | 9.5 | 2.10, s | | C4', C5', C6' | H7' |
| 6-OH | | 10.05, s | | C1, C5, C6 | H7, 2'-OH, 6'-OH |
| 2'-OH | | 15.86, s | | C1', C3', C8' | 6-OH |
| 6'-OH | | 11.41, s | | C1', C5', C6' | H7, 6-OH |

These findings suggest that 2 is an analogue of 1 with different structure of the side chains. Interpretation of COSY and HMBC experiments, especially HMBC correlations observed with the two ketonic carbons at $\delta_c$ 208.0 (C8) and $\delta_c$ 207.5 (C8), easily revealed the presence of valeryl and butyryl chains. The connection of the valeryl side chain to the acylfilicinic acid moiety was determined with HMBC correlation between the protons of the methylene H9 at $\delta_H$ 3.19 with the quaternary carbon C3 at $\delta_c$ 108.9 ppm. The allocation of the butyryl chain was established with the ROESY experiment (data not shown). In fact, the protons of the methylene H9 at $\delta_H$ 3.15 displayed a ROE correlation with the protons of the methoxyl H7 at $\delta_H$ 3.80, which exhibited a clear ROE correlation with the toluene methyl H12 at $\delta_H$ 2.10.

The structure determined with the NMR data was confirmed by single-crystal X-ray diffraction analysis (See Tables S9-S16). Crystallographic data were recorded at 150 K to reduce agitation induced by the length of the valeryl side chain. Compound 2 was named Aspidin CB; this is the first time that this compound was isolated and characterized.

III - Isolation of Compounds from SFE-$CO_2$ Extracts from Psiloxylon mauritianum A 1.0 g of dry plant powder was weighed and used for extraction. Different co-solvent percentages of ethanol from 0, 1, 2 and 5% and a back pressure of 200 bars were applied for 15 min, with a flow rate of 2 mL.min$^{-1}$. Each fraction resulted from the different percentages of ethanol were concentrated to dryness under reduced pressure and the yield was calculated (table 2)

TABLE 2

SFE conditions and yields for the fractions of P. mauritianum leaves extraction

| Solvent | Percentage (v/v) (%) | Mass (mg) | Yields (%) |
|---|---|---|---|
| $CO_2$ | 100 | 44.3 mg | 4.4% |
| $CO_2$/EtOH | 99/1 | 4.9 mg | 0.5% |
| $CO_2$/EtOH | 98/2 | 3.7 mg | 0.4% |
| $CO_2$/EtOH | 95/5 | 6.0 mg | 0.6% |

Figure 2:
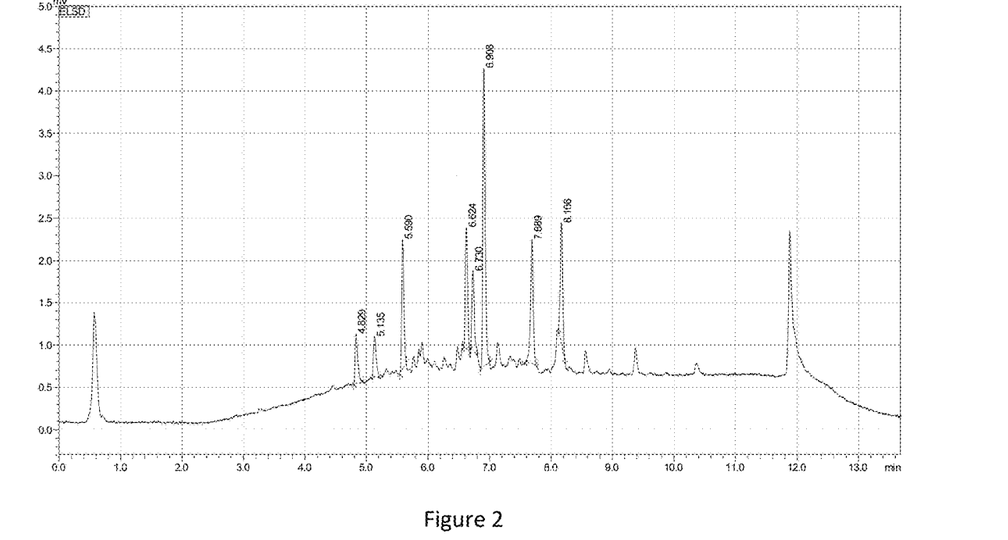
FIG. 2. Chromatographic profiles SFE extract obtained with 100% $CO_2$.

The fraction obtained with $CO_2$ 100% was subjected to UHPLC analysis and the presence of aspidin BB (RT=7.69 min) and aspidin CB (RT=8.17 min) was determined by comparison of retention times. (Cf FIG. 2)

IV. Antibacterial Properties

Antibacterial properties of Crude Extracts from Psiloxylon mauritianum

All Crude extracts obtained from P. mauritianum (leave and stem) have exhibited significant bacterial inhibition, particularly on *S. aureus*. (Table 3). An alteration of the growth was observed for *C. albicans* and *P. aeruginosa* even at low concentration.

TABLE 3

Antimicrobial results for crude extracts of leaves and stems from *P. mauritianum*

| | MIC (µg/ml) | |
|---|---|---|
| Extract | *S. aureus* ATCC 29213 | *T. rubrum* SNB-TR1 |
| Leaves | | |
| AcOEt | 16-32 | 256 |
| MeOH | 8-16 | 128 |
| Water | 8-16 | 128 |
| Stems | | |
| AcOEt | 512-256 | 128 |
| MeOH | 512-256 | 32 |
| Water | 8-16 | 128 |

Antibacterial Properties of Crude Extracts of Leaves from *P. mauritianum* against Gram Negative Pathogens Bacterial growth kinetics of *Acinetobacter baummanii* 19606, *Escherichia coli* WT 25922 and *Klebsiella pneumoniae* WT 700603 incubated with crude extracts of *P. mauritianum* at 32 µg/ml were followed during a period of 16 hours. Kinetic curves allowed us to establish that the growth of bacteria was inhibited with all extracts, compared to the negative control, at the test concentration. Crude methanolic and water extracts of *P. mauritianum* have shown a significant inhibition of *Acinetobacter baummanii* 19606 at 32 µg/ml.

Antibacterial Properties Aspidin CB Against Gram-Positive Pathogens

Aspidin CB exhibited strong antibacterial activity against standard and methicillin-resistant *S. aureus* strains, with a minimal inhibition concentration (MIC) of 0.25 µg/mL, and no cytotoxicity was observed at $10^{-5}$ M in MRC5 cells. Similar Anti-SARM activities were also observed against SARM clinical strains. Our results suggested also potent antibacterial activity against other Gram-positive pathogens. (Table 4)

Furthermore, similar antibacterial properties were observed for different clinical strains of *Staphylococcus*, such as *Staphylococcus hominis*, *Staphylococcus argenteus*, *Staphylococcus haemolyticus*, *Staphylococcus warnieri*, *Staphylococcus lugdunensis*.

TABLE 4

Examples of antimicrobial results for Aspidin CB againt Gram-positive bacteria

| Bacteria | MIC (µg/ml) | Bacteria | MIC (µg/ml) |
|---|---|---|---|
| *S. epidermis* MSF G + 15* | 0.5 | SARM G + 82* | 0.5 |
| SARM NCTC 12493 | 0.5 | SARM G + 86* | 0.5 |
| *S. aureus* ATCC25923 | 0.5 | *Enterococcus faecalis* 29212 | 8 |
| SARM G + 78* | 0.5 | *Enterococcus faecium* van B* | 0.5 |
| SARM G + 79* | 1 | *S. epidermis* MSF G + 16* | 2 |

TABLE 4-continued

Examples of antimicrobial results for Aspidin CB againt Gram-positive bacteria

| Bacteria | MIC (µg/ml) | Bacteria | MIC (µg/ml) |
|---|---|---|---|
| *Bacillus* sp. L4 210321* | 1 | *Enterococcus faecium* SI299* | 8 |
| *Corynebacterium* sp. L2 220321* | 1 | | |

*Clinical strain

Antibacterial Properties of Aspidin CB Against Gram-Negative Pathogens

Gram-negative bacteria possess a unique outer membrane that makes them resistant to several antimicrobial agents. Permeabilizers are compounds that weaken the outer membrane by enhance the permeability of bacterial cells to antimicrobial agents. [Farrag, H. A.; Abdallah, N.; Shehata, M. M. K.; Awad, E. M. J Biomed Sci, 2019, 26:69] Colistin a.k.a. polymyxin E were extensively used in clinical practice for Gram-negative organisms, but gradually withdrawn from the market due to reports of significant nephrotoxicity and neurotoxicity. [Mohamed, Y. F., Abou-Shleib, H. M., Khalil, A. M., El-Guink, N. M., & El-Nakeeb, M. A. Braz J Microbiol., 2016, 47, 381-388] In combinaison with various antibiotics, colistin is known to destabilize the outer membrane enhancing the antibacterial activity. In our study, we evaluated a combinaison of colistin at a sub-inhibitory concentration and Aspidin CB. The results have showed that Aspidin CB was unambiguously more active against *A. baumanii* and *E. coli* in a combination with colistin. (Table 5)

TABLE 5

Antimicrobial results for Aspidin CB in combination with colistin againt Gram-negative bacteria MIC (µg/ml)

| | *Escherichia coli* WT 25922 | *Acinetobacter baummanii* 19606 |
|---|---|---|
| Aspidin CB | >64 | >64 |
| Colistin | 1 | 4 |
| Aspidin CB+ colistine 0.25 µg/ml | 16 | >64, altered growth |
| Aspidin CB+ colistine 0.50 µg/ml | n.d. | 32 |
| Negative control (DMSO) | >64 | >64 | n.d. not determined

Other experiments performed with both EtOAc crude extract and isolated compounds are presented in Table 6 and confirm previous results.

TABLE 6

Antimicrobial and cytotoxic results for EtOAc crude extract and isolated compounds.

|  | MIC (µg/mL) | | | | MRC5 Cell Viability (%) | |
| --- | --- | --- | --- | --- | --- | --- |
|  | C. albicans | T. rubrum | S. aureus | MRSA | | |
| Compounds | ATCC 10213 | SNB-TR1 | ATCC 29213 | ATCC 33591 | $10^{-5}$ M | $10^{-6}$ M |
| 1 | >256 | >256 | 2 | 1 | 86 ± 3 | 104 ± 1 |
| 2 | >256 | 256 | 0.25 | 0.25 | 99 ± 2 | 105 ± 2 |
| Crude extract | 8 | 256 | 8 | nd | 96 ± 2 | 100 ± 3 |
| Fluconazole[1] | 1 | 4 | nd | nd | nd | nd |
| Itraconazole[1] | <0.5 | <0.5 | nd | nd | nd | nd |
| Oxacillin[1] | nd[2] | nd | 0.25 | nd | nd | nd |
| Vancomycin[1] | nd | nd | nd | 4 | nd | nd |

[1]Positive control.
[2]Not determined.

Compounds 1 and 2 exhibited antibacterial activity against *S. aureus* and MRSA higher than the positive control, with MICs of 0.25 µg/mL for 2 and 2 and 1 µg/m L for 1, respectively, against these two pathogens. Our results indicated that compound 2 has the same MIC as oxacillin against *S. aureus* and was 16-fold more potent than the standard antibiotic vancomycin against MRSA. Interestingly, Aspidin CB (2) showed higher activity than compound 1 against both bacteria. Furthermore, no cytotoxicity was observed for compound 2 at concentrations up to $10^{-5}$ M (Table 2). In our assays, Aspidin CB (2) was more active against MRSA and slightly less toxic than 1, which is known to exhibit no toxicity when *S. aureus* was killed.

In accordance with the literature, Aspidin BB (1) was strongly active against both *S. aureus* and MRSA but was inactive against the human pathogenic fungi. Aspidin BB (1) is known to exert strong antibacterial activity against Gram-positive bacteria, like *S. aureus, S. epidermis* or *Propionibacterium acnes* Li et al. identified the relationship between antibacterial activity and increase levels of reactive oxygen species in *S. aureus* cells. Moreover, the authors demonstrated that 1 induced peroxidation of membranes, DNA damage and protein degradation in *S. aureus*. By comparing the effects of compounds 1 and 2 on *S. aureus* strains, our results demonstrated that a longer carbon chain (2 additional carbons) on the acylfilinic acid moiety is correlated with 4-to 8-fold stronger activity (Table 2). Compared to Aspidin BB (1), the antibacterial potency of Aspidin CB (2) may result from better cell wall penetration due to a longer alkyl chain inducing improved lipophilicity.

IV. Cosmetic Applications of AcOEt and MeOH extracts of *P. mauritianum*

Antioxidant Properties

It was found that AcOEt and MeOH extracts of *P. mauritianum* leaves and stems possessed significant antioxidant capacities compared to positive controls (trolox and tocopherol). (Table 7) HPLC chromatograms of water and MeOH extracts of *P. mauritianum* (leaves and stems) were very similar and suggested a similar composition.

TABLE 7

Radical scavenging capacity of *P. Mauritianum* extracts at 50 µg/ml.

|  | % ABTS inhibition |
| --- | --- |
| EtOAC leaves extract | 77.5 |
| MeOH leaves extract | 97.6 |
| EtOAC stems extract | 83.2 |
| MeOH stems extract | 97.8 |
| Tocopherol | 97.6 |
| Trolox | 98.0 |

Antibacterial Properties

The water extract of *P. mauritianum* leaves has clearly showed a preservative efficacy in a cleansing milk. (table 8)

TABLE 8

Challenge test results for cleansing milk formulated with 3% of *P. mauritianum* leave water extract.

|  | Log reduction at (days) | | | | |
| --- | --- | --- | --- | --- | --- |
| Organisms | 0 | 2/5 | 7/12 | 14/19 | 28/29 |
| Staphylococcus aureus | 6.00 | >4.00 | >4.00 | >4.00 | >4.00 |
| Escherichia coli | 6.38 | 0.57 | >3.38 | >4.38 | >4.38 |
| Pseudomonas aeruginosa | 6.59 | >4.57 | >4.57 | >4.57 | >4.57 |

A part of the description of the invention, especially regarding experimental part, is also available in the article: *Potent and Non-Cytotoxic Antibacterial Compounds against Methicillin-Resistant Staphylococcus aureus Isolated from Psiloxylon mauritianum, A Medicinal Plant from Reunion Island* published in Molecules in August 2020. DOI: 10.3390/molecules25163565

The invention claimed is:

1. A method of treating a microbial infection, the method comprising administering a composition comprising an isolated aspidin of formula (II)

to a patient in need thereof.

2. The method according to claim 1, wherein said microbial infection is a bacterial infection.

3. The method according to claim 2, wherein said bacterial infection is an infection by a gram-positive bacterial strain.

4. The method according to claim 3, wherein said gram-positive bacterial strain is chosen from *Staphylococcus aureus, Staphylococcus epidermidis, Staphylococcus hominis, Staphylococcus argenteus, Staphylococcus haemolyticus, Staphylococcus warnieri, Staphylococcus lugdunensis, Corynebacterium diphteriae, Corynebacterium minutissimum, Corynebacterium acnes (Propionibacterium acnes), Corynebacterium sp., Bacillus cereus, Bacillus subtilis, Bacillus anthracis, Bacillus sp., Enterococcus faecium, Enterococcus faecalis, Enterococcus sp., Nocardia abscessus, Nocardia farcinica, Nocardia asteroides, Nocardia cyriacigeorgica, Nocardia brasiliensis, Nocardia brevicatena, Nocardia paucivorans, Nocardia nova, Nocardia transvalensis, Nocardia sp., Streptococcus pyogenes, Streptococcus agalactiae, Streptococcus pneumoniae, Streptococcus mutans*, and *Streptococcus* sp.

5. The method according to claim 4, wherein said *Staphylococcus aureus* strain is a methicillin-resistant *Staphyloccocus aureus* or a vancomycin-resistant *Staphyloccocus aureus*.

6. The method according to claim 2, wherein the bacterial strain is a gram-negative bacterial strain.

7. The method according to claim 6, wherein said gram-negative bacterial strain is chosen from *Escherichia coli, Klebsiella pneumoniae, Acinetobacter baumannii, Pseudomonas aeruginosa*, and *Enterobacter* spp.

8. The method according to claim 6, further comprising administering at least one outer membrane permeabilizer.

9. The method of claim 8, wherein the at least one outer membrane permeabilizer is a polymyxin.

10. The method of claim 9, wherein the polymyxin is colistin.

11. The method according to claim 1, wherein the microbial infection is a fungal infection selected from the group consisting of *Candida albicans, Candida parapsilosis, Candida glabrata, Candida tropicalis, Cryptococcus neoformans, Cryptococcus gatti, Pneumocystis jirovecii, Aspergillus fumigatus, Aspergillus flavus, Aspergillus nidulans, Aspergillus versicolor, Aspergillus niger, Aspergillus terreus, Histoplasma capsulatum, H. capsulatum duboisii*, and *Torulopsis glabrata*.

* * * * *